United States Patent [19]

Malen et al.

[11] Patent Number: 5,494,934

[45] Date of Patent: Feb. 27, 1996

[54] GUANIDINE COMPOUNDS

[75] Inventors: Charles Malen, Fresnes; Jean-Michel Lacoste, Sevres; Guillaume de Nanteuil, Suresnes, all of France

[73] Assignee: Adir et Compagnie, Courbevoie, France

[21] Appl. No.: 787,374

[22] Filed: Nov. 4, 1991

[30] Foreign Application Priority Data

Nov. 29, 1990 [FR] France .................. 90 14898

[51] Int. Cl.⁶ .................................. A61K 31/155
[52] U.S. Cl. .............. 514/632; 514/256; 514/275; 514/392; 514/398; 514/401; 514/631; 514/634; 544/330; 544/332; 548/331.5; 564/227; 564/228; 564/230; 564/237
[58] Field of Search ................. 364/227, 228, 364/230, 237; 514/632, 634

[56] References Cited

U.S. PATENT DOCUMENTS

| | | | |
|---|---|---|---|
| 3,658,993 | 4/1972 | Kodama et al. | 514/632 |
| 3,916,531 | 6/1974 | Bruce et al. | 564/228 |
| 4,341,782 | 7/1982 | Konishi et al. | 544/330 |
| 4,665,085 | 5/1987 | Cocquelet et al. | 564/228 |
| 4,731,393 | 3/1988 | Erczi et al. | 564/228 |
| 5,010,082 | 4/1991 | Riebli | 544/330 |

FOREIGN PATENT DOCUMENTS

| | | | |
|---|---|---|---|
| 3416695 | 10/1985 | Germany | 564/228 |
| 115330 | 9/1979 | Japan | 514/632 |

Primary Examiner—Glennon H. Hollrah
Assistant Examiner—Scott C. Rand
Attorney, Agent, or Firm—Gordon W. Hueschen

[57] ABSTRACT

A compound of formula (I):

$$\begin{array}{c}R_1\\ \phantom{x}\diagdown\\ \phantom{xx}C-A-NH-C\\ \diagup\phantom{x}|\\ R_2\phantom{x}R\end{array}\begin{array}{c}N-R_3\\ \diagup\diagup\\ \\ \diagdown\\ NH-R_4\end{array} \quad (I)$$

in which:

$R_1$ represents substituted or unsubstituted phenyl or $(C_3-C_7)$ cycloalkyl, $R_2$ represents trifluoromethyl or $(C_3-C_4)$ cycloalkyl, A represents $—CH_2—$, $—CH=N—$, $=N—$ or $—NH—$, $R_3$ and $R_4$, which may be identical or different, represent hydrogen or linear or branched $(C_1-C_6)$ alkyl or, with the nitrogen atoms to which they are attached, form a 5- or 6-membered heterocycle, R represents either hydrogen in the case where $A=—CH_2—$, $—CH=N—$ or $—NH—$, or a bond of the group A when the latter is equal to $=N—$, its enantiomers and epimers as well as its addition salts with a pharmaceutically acceptable acid.

Medicine products.

7 Claims, No Drawings

GUANIDINE COMPOUNDS

The present invention relates to new guanidine compounds.

Numerous acyclic guanidine compounds, 2-aminoimidazoline compounds, better defined as cyclic guanidines, and also imidazoline compounds have been described in the literature. Most of these molecules display affinities for $\alpha_2$-adrenoceptors.

Now, it was demonstrated recently that there existed specific "imidazoline-guanidine" receptors, different from $\alpha_2$-adrenoceptors, both at central nervous system level and at peripheral level (P. Bousquet et al. Eur. J. Pharmacol., 150(3), 401, 1988 and A. Parini et al. J. Biol. Chem., 264(20), 11874, 1989).

The compounds of the present invention, besides the fact that they are new, display a quite specific affinity for these "imidazoline-guanidine" receptors, which can also be called "endazoline" receptors. This affinity is all the more advantageous for the fact that it is accompanied by a very great selectivity, not only with respect to $\alpha_1$- and $\alpha_2$-adrenoceptors but also with respect to 5-HT receptors.

The presence of "endazoline" receptors at central nervous system level, at hepatic level, at adipose tissue level and also at pulmonary level hence renders the compounds of the invention usable as an agonist or antagonist with respect to these receptors, not only in the treatment of depression, arterial hypertension and vascular disorders but also in the treatment of diabetes, obesity and pulmonary diseases.

The invention relates more specifically to new guanidine compounds corresponding to the general formula (I):

$$\begin{array}{c} R_1 \\ \phantom{R}\diagdown \\ \phantom{RR}C-A-NH-C \\ \phantom{R}\diagup\ | \phantom{-A-NH-C}\diagdown \\ R_2 \phantom{\diagup} R \phantom{-A-NH-}NH-R_4 \end{array} \quad \text{with } N=R_3 \text{ double bond} \qquad (I)$$

in which:
R$_1$ represents
— a phenyl group optionally substituted with one or more halogen atoms or linear or branched (C$_1$–C$_6$) alkyl, hydroxyl or linear or branched (C$_1$–C$_6$) alkoxy groups,
— a cycloalkyl group containing from 3 to 7 carbon atoms,
R$_2$ represents a trifluoromethyl group or a cycloalkyl group containing from 3 to 4 carbon atoms,
A represents a —CH$_2$—, —CH=N—, =N— or —NH— group,
R$_3$ and R$_4$, which may be identical or different, represent a hydrogen atom or a linear or branched (C$_1$–C$_6$) alkyl group or, with the nitrogen atoms to which they are attached, form a 5- or 6-membered heterocycle,
R represents either a hydrogen atom in the case where A represents a —CH$_2$—, —CH=N— or —NH— gorup, or a bond of the group A when the latter is represented by =N—, with the proviso, however, that when A is =N— and R$_1$ is a phenyl optionally substituted, R$_2$ does not represent a cycloalkyle (C$_3$–C$_4$).

their enantiomers and epimers as well as their addition salts with a pharmaceutically acceptable acid.

Among pharmaceutically acceptable acids, hydrochloric, sulfuric, tartaric, maleic, fumaric, methanesulfonic and camphoric acids, and the like, may be mentioned without implied limitation.

The invention also encompasses the process for preparing the compounds of formula (I), wherein a ketone of formula (II):

$$\begin{array}{c} R_1 \\ \phantom{R}\diagdown \\ \phantom{RR}C=O \\ \phantom{R}\diagup \\ R_2 \end{array} \qquad (II)$$

in which R$_1$ and R$_2$ have the same meaning as in the formula (I), is used as the starting material, which ketone is subjected
1/either
to the action of a compound of formula (III) in an organic solvent $$H_2N-NH-C\begin{array}{c}\diagup N-R_3 \\ \diagdown NH-R_4\end{array} \qquad (III)$$

in which R$_3$ and R$_4$ have the same meaning as in the formula (I), to yield a compound of formula (I/a), a special case of the compounds of formula (I)

$$\begin{array}{c} R_1 \\ \phantom{R}\diagdown \\ \phantom{RR}C=N-NH-C\begin{array}{c}\diagup N-R_3 \\ \diagdown NH-R_4\end{array} \\ \phantom{R}\diagup \\ R_2 \end{array} \qquad (I/a)$$

in which R$_1$, R$_2$, R$_3$ and R$_4$ have the same meaning as in the formula (I), A represents a =N— group and R a bond of this group, which is subjected, if so desired, to the action of an alkali metal hydride, to yield the compounds of formula (I/b)

$$\begin{array}{c} R_1 \\ \phantom{R}\diagdown \\ \phantom{RR}CH-NH-NH-C\begin{array}{c}\diagup N-R_3 \\ \diagdown NH-R_4\end{array} \\ \phantom{R}\diagup \\ R_2 \end{array} \qquad (I/b)$$

in which R$_1$, R$_2$, R$_3$ and R$_4$ have the same meaning as in the formula (I), A represents an —NH— group and R a hydrogen atom,
2/or
to the action of methoxymethyltriphenylphosphonium chloride in the presence of a strong base to yield the enol ether of formula (IV)

$$\begin{array}{c} R_1 \\ \phantom{R}\diagdown \phantom{RRR} OCH_3 \\ \phantom{RR}CH=C \\ \phantom{R}\diagup \phantom{RRR}\diagdown H \\ R_2 \end{array} \qquad (IV)$$

in which R$_1$ and R$_2$ have the same meaning as in the formula (I), which is hydrolyzed in an acid medium to yield the aldehyde of formula (V)

$$\begin{array}{c} R_1 \\ \phantom{R}\diagdown \\ \phantom{RR}CH-CHO \\ \phantom{R}\diagup \\ R_2 \end{array} \qquad (V)$$

in which R$_1$ and R$_2$ have the same meaning as in the formula (I), which is subjected either
to the action of a compound of formula (III)

$$H_2N-NH-C\begin{array}{c}\diagup N-R_3 \\ \diagdown NH-R_4\end{array} \qquad (III)$$

in which R$_3$ and R$_4$ have the same meaning as in the formula (I), to yield a compound of formula (I/c), a special case of the compounds of formula (I)

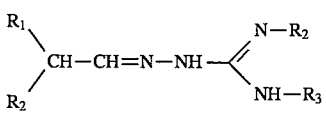

in which $R_1$, $R_2$, $R_3$ and $R_4$ have the same meaning as in the formula (I), A represents a —CH=N— group and R a hydrogen atom, or to the action of a compound of formula (VI) in the presence of pyridine $$H_2N\ O-R' \quad\quad (VI)$$

in which R' represents a hydrogen atom or a ($C_1$–$C_6$) alkyl group, to yield a compound of formula (VII)

in which $R_1$, $R_2$ and R' have the same meaning as above, which is reduced by catalytic hydrogenation or in the presence of an alkali metal mixed hydride, to yield an amine or formula (VIII)

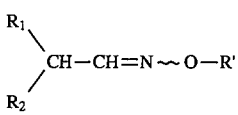

in which $R_1$ and $R_2$ have the same meaning as in the formula (I), which is subjected to the action of a compound of formula (IX)

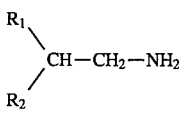

in which $R_3$ and $R_4$ have the same meaning as in the formula (I), to yield a compound of formula (I/d), a special case of the compounds of formula (I)

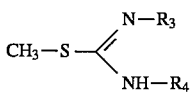

in which $R_1$, $R_2$, $R_3$ and $R_4$ have the same meaning as in the formula (I), A represents a —$CH_2$— gorup and R a hydrogen atom, which compounds of formulae (I/a), (I/b), (I/c) and (I/d) collectively constitute the compounds of formula (I), which are purified, where appropriate, by conventional purification techniques, the isomers of which are separated, if so desired, by conventional separating techniques and which are converted, if necessary, to their addition salts with a pharmaceutically acceptable acid.

The subject of the present invention is also pharmaceutical compositions containing as active principle at least one compound of general formula (I) or one of its addition salts with a pharmaceutically acceptable acid, alone or in combination with one or more non-toxic, inert excipients or vehicles.

Among the pharmaceutical compositions of the invention, there may be mentioned, more especially, those which are suitable for oral, parenteral and nasal administration, simple or sugar-coated tablets, sublingual tablets, sachets, packets, hard gelatin capsules, sublingual preparations, troches, suppositories, creams, ointments, skin gels, and the like.

The appropriate dosage varies according to the patient's age and weight, the nature and severity of the condition and also the administration route. The latter can be oral, nasal rectal or parenteral. Generally speaking, single doses range between 0.1 and 100 mg for a treatment administered in 1 to 3 doses per 24 hours.

The examples which follow illustrate the invention and in no way limit it.

EXAMPLE 1

2,2-Dicyclopropylethylidene)hydrazino-2-imidazoline

STAGE A: Dicyclopropylacetaldehyde 0.77 mol of dicyclopropyl ketone is added rapidly under a nitrogen atmosphere to a suspension of 1.2 mol of sodium hydride in 1.4 liters of dimethyl sulfoxide.

1.2 mol of trimethylsulfonium iodide are then added to this mixture, which is stirred for one hour at room temperature, then 1 h 30 min at 60° C. and finally 1 hour at 80° C. After cooling, the mixture is poured into 3 liters of ice-cold water and the pH is taken to 6–7 with concentrated hydrochloric acid.

A steam distillation yields a distillate, which is saturated with 450 g of sodium chloride. After extraction with ether and evaporation, the expected product is obtained by distillation.

Boiling point: 64°–66° C. (15 mm/Hg)

Yield: 37%

STAGE B:
(2,2-Dicyclopropylethylidene)hydrazino-2-imidazoline 50 mmol of the product obtained in the preceding stage and 50 mmol of 2-hydrazino-2-imidazoline hydriodide are reacted in 40 ml of ethanol. After 5 hours under reflux, the solvent is evaporated off. The residue is taken up with 20 ml of water and 7 ml of 10N sodium hydroxide.

After extraction with three times 50 ml of methylene chloride, drying and evaporation of the solvent, the expected product is obtained after recrystallization in water.

Yield: 78%

Melting point: 124°–127° C.

Elemental microanalysis:

|  | C % | H % | N % |
|---|---|---|---|
| calculated | 64.05 | 8.80 | 27.16 |
| found | 63.75 | 8.75 | 27.15 |

EXAMPLE 2

(2,2-Dicyclopropylethylidene)aminoguanidine hydrochloride

The expected product is obtained using the procedure described in Example 1, but replacing 2-hydrazino-2-imidazoline hydriodide in stage B by aminoguanidine hydrochloride and leaving the mixture under reflux for 15 minutes.

After cooling and evaporation of the solvent, the residue is recrystallized in acetonitrile.

Yield: 65%

Melting point: 168°–170° C.

Elemental microanalysis:

|            | C %   | H %  | N %   | Cl %  |
|------------|-------|------|-------|-------|
| calculated | 49.88 | 7.91 | 25.85 | 16.36 |
| found      | 50.22 | 8.14 | 26.17 | 16.38 |

EXAMPLE 3

(2,2-Dicyclopropylethylamino)-2-imidazoline hydriodide

Stage A is identical to stage A of Example 1.

STAGE B: Dicyclopropylacetaldehyde oxime 520 mmol of product obtained in the preceding stage, dissolved in 60 ml of ethanol, are poured rapidly into a solution containing 520 mmol of hydroxylamine hydrochloride and 27 mmol of sodium carbonate in 100 ml of water. The mixture is brought to reflux for 30 minutes and then left for 2 hours at room temperature.

The aqueous phase is saturated with sodium chloride after separation when settling has taken place, and extracted 3 times with 60 ml of ether. The organic phases are combined, dried and evaporated. The expected product is obtained by distillation.

Boiling point: 110°–112° C. (15 mm Hg)
Yield: 85%

STAGE C: 2,2-Dicyclopropylethylamine hydrochloride 540 mmol of the product obtained in the preceding stage, dissolved in 140 ml of anhydrous ether, are poured into a suspension containing 860 mmol of lithium aluminum hydride in 1.4 liters of anhydrous ether.

After 3 hours under reflux, the reaction mixture is hydrolyzed with 20 ml of water and then 17 ml of 20% sodium hydroxide and finally with 76 ml of water.

The precipitate obtained is filtered off and rinsed with ether. The expected product in the form of a base is obtained after evaporation of the solvent. It is converted to a hydrochloride by the action of ethereal hydrogen chloride.

Yield: 67%
Melting point: 140°–142° C.
Elemental microanalysis:

|            | C %   | H %  | N %  | Cl %  |
|------------|-------|------|------|-------|
| calculated | 59.43 | 9.99 | 8.68 | 21.94 |
| found      | 59.42 | 9.65 | 8.54 | 22.04 |

STAGE D:
(2,2-Dicyclopropylethylamino)-2-imidazoline hydriodide 60 mmol of the products obtained in the preceding stage and 60 mmol of 2-methylthioimidazoline hydriodide are brought to 100° C. in 30 ml of dimethylformamide under a nitrogen atmosphere for 8 hours.

The expected product is obtained after evaporation of the solvent and crystallization in the cold state.

Yield: 74%
Melting point: 87°–93° C.

Elemental microanalysis:

|            | C %   | H %  | N %   |
|------------|-------|------|-------|
| calculated | 41.15 | 6.28 | 13.09 |
| found      | 40.98 | 6.35 | 13.08 |

EXAMPLE 4

(Dicyclopropylmethylene)hydrazino-2-imidazoline

Using the procedure described in stage B of Example 1, but replacing dicyclopropylacetaldehyde by dicyclopropyl ketone and leaving the reaction mixture under reflux overnight, the expected product is obtained.

Recrystallization solvent: acetonitrile
Yield: 70%
Melting point: 120°–124° C.
Elemental microanalysis:

|            | C %   | H %  | N %   |
|------------|-------|------|-------|
| calculated | 62.47 | 8.39 | 29.12 |
| found      | 62.40 | 8.30 | 28.91 |

EXAMPLE 5

(2-Cyclopentyl-3,3,3-trifluoropropylidene)amioguanidine hydrochloride

STAGE A: Cyclopentyl trifluoromethyl ketone

A suspension of sodium trifluoroacetate, prepared by adding 0.5 mol of trifluoroacetic acid dissolved in THF slowly at 0° C. to 0.5 mol of sodium hydride suspended in THF, is added to an organomagnesium reagent, itself prepared by the dropwise addition under continuous reflux of 0.5 mol of cyclopentyl bromide dissolved in 400 ml of ethyl ether to 13.4 g of magnesium turnings placed in 50 ml of anhydrous ethyl ether with an iodine crystal, refluxing being maintained for one hour.

The white suspension thereby obtained is brought to reflux for 20 hours 30 minutes and kept overnight at room temperature.

The mixture is then hydrolyzed at 0° C. with 200 ml of 6N hydrochloric acid and 250 ml of water.

The organic phase is then washed with water, thereafter with 10% bicarbonate solution and again with water.

After drying and evaporation of the solvents, the expected product is obtained by distillation.

Boiling point: 60°–65° C. (150 mm/Hg)

STAGE B:
1-Methoxy-2-cyclopentyl-3,3,3-trifluoropropene

A solution containing 211 g of methoxymethyltriphenylphosphonium chloride in 120 ml of anhydrous tetrahydrofuran is added to a solution of lithium diisopropylamide (prepared by adding 400 ml of n-butyllithium (1.6M) in hexane at −10° C. over 30 minutes to a solution containing 78.5 ml of freshly distilled diisopropylamine in 120 ml of tetrahydrofuran) while the temperature is maintained below 0° C.

A solution containing 64 g of the product obtained in the preceding stage in 120 ml of tetrahydrofuran is then added to the above mixture at a temperature below 0° C. over 30 minutes.

The resulting mixture is stirred at room temperature for 72 hours and then filtered. The solvent is evaporated off and the expected product is obtained after distillation of the residue under vacuum.

Yield: 50%

Melting point: 80°–87° C. (40 mm/Hg)

STAGE C: Cyclopentyltrifluoromethylacetaldehyde 15 ml of concentrated sulfuric acid are added dropwise and with stirring at a temperature of between 0° and 3° C. to a suspension of 180 mmol of the product obtained in the preceding stage in 60 ml of water.

The mixture is kept stirring for 4 hours at room temperature. After extraction with 30 times 50 ml of ether, washing of the organic phases with water, drying and evaporation of the solvent, the expected product is obtained by distillation under vacuum.

Boiling point: 72°–74° C. (50 mm/Hg)

STAGE D: (2-Cyclopropyl-3,3,3-trifluoropropylidene)aminoguanidine hydrochloride

A solution containing 5.6 mmol of the product obtained in the preceding stage and 5.6 mmol of aminoguanidine hydrochloride in 10 ml of anhydrous ethanol is brought to reflux for 30 minutes. After cooling and evaporation of the solvent, the expected product is obtained and is recrystallized in toluene.

Yield: 60%

Melting point: 107°–109° C.

Elemental microanalysis:

|  | C % | H % | N % | Cl % |
| --- | --- | --- | --- | --- |
| calculated | 39.64 | 5.91 | 20.54 | 13.00 |
| found | 39.47 | 5.88 | 20.66 | 13.14 |

EXAMPLE 6

(2-Phenyl-3,3,3-trifluoropropylidene)aminoguanidine hydrochloride

Using the procedure described in Example 5 (stages B to D), but replacing cyclopentyl trifluoromethyl ketone in stage B by phenyl trifluoromethyl ketone, the expected product is obtained.

Yield:

Melting point: 117°–120° C.

Elemental microanalysis:

|  | C % | H % | N % | Cl % |
| --- | --- | --- | --- | --- |
| calculated | 42.79 | 4.31 | 19.96 | 12.63 |
| found | 42.93 | 4.35 | 19.83 | 12.45 |

EXAMPLE 7

(2-(2-Phenyl-3,3,3-trifluoro-1-propylamino)imidazoline fumarate

STAGE A: 1-Methoxyimino-2-phenyl-3,3,3-trifluoropropane

A mixture containing 40 mmol of phenyltrifluoromethylacetaldehyde, 43 mmol of O-methylhydroxylamine hydrochloride and 100 ml of distilled pyridine in 100 ml of anhydrous ethanol is brought to reflux for 2 hours. After evaporation of the solvent under reduced pressure at a temperature below 25° C., the residue is treated with 50 ml of water and extracted with 3 times 50 ml of ether.

The expected product is then obtained after drying and evaporation of the ether phase and distillation under vacuum.

Yield: 96%

Boiling point: 108°–110° C. (22 mg/Hg)

STAGE B: 2-Phenyl-3,3,3-trifluoropropylamine 115 ml of a molar solution of diborane in tetrahydrofuran are added to a solution, cooled to 5° C., containing 38 mmol of the product obtained in the preceding stage in 30 ml of anhydrous tetrahydrofuran while the temperature is maintained below 10° C.

The mixture is then brought to reflux for 3 hours, cooled to 20° C., thereafter treated with 40 ml of methanol and again brought to reflux for 3 hours. After cooling, the solvents are evaporated off under reduced pressure at a temperature below 25° C.

The residue is taken up with 30 ml of ether, filtered off and treated with an ethereal hydrogen chloride solution. The hydrochloride thereby obtained is then treated with sodium hydroxide and the expected product is obtained after extraction with ether, drying and evaporation of the solvent and distillation under vacuum.

Yield: 85%

Boiling point: 105°–110° C. (18 mm/Hg)

STAGE C: 2-(2-Phenyl-3,3,3-trifluoro-1-propylamino)imidazoline fumarate 14.5 mmol of the product obtained in the preceding stage and 14.5 mmol of 2-mercapto-4,5-dihydroimidazole hydriodide in 20 ml of anhydrous dimethylformamide are brought to reflux for 12 hours.

After cooling and evaporation of the solvent, the residue is dissolved in 2 ml of water, treated with 2 ml of sodium hydroxide (35%) and extracted with 3×15 ml of ether. After washing of the ether phases with water, drying and evaporation, the expected product is obtained in the form of a fumarate by treating the oil with 10 mmol of fumaric acid in 50 ml of ethanol, evaporation and recrystallization in isopropanol.

Yield: 53%

Melting point: 132°–134° C.

Elemental microanalysis:

|  | C % | H % | N % |
| --- | --- | --- | --- |
| calculated | 51.48 | 4.86 | 11.26 |

|   | C % | H % | N % |
|---|---|---|---|
| found | 51.17 | 4.79 | 11.19 |

PHARMACOLOGICAL STUDY OF THE COMPOUNDS OF THE INVENTION

EXAMPLE 8

In vitro affinity test for endazoline, $\alpha_1$ and $\alpha_2$ and 5-HT receptors The in vitro affinity tests for endazoline receptors were carried out according to a technique described by A. Parini et al. (Biochem. and Biophys. Res. Comm. 147(3), 1055, 1987), and according to conventional binding techniques for the other receptors.

The results of these studies show, in particular, that the compound of Example 2 possesses a $K_i$ of the order of $10^{-8}$M with respect to endazoline receptors, and of the order of:

$2\times10^{-6}$ with respect to $\alpha_2$-andrenoceptors greater than $10^{-4}$ with respect to $\alpha_1$-adrenoceptors $10^{-5}$ with respect to 5-$HT_{1A}$ receptors $10^{-4}$ with respect to 5-$HT_{1B}$ receptors $2\times10^{-5}$ with respect to 5-$HT_2$ receptors $2\times10^{-6}$ with respect to 5-$HT_3$ receptors.

These results show not only the affinity of the compound for endazoline receptors, but also the great selectivity with respect to the other receptors tested.

PHARMACEUTICAL COMPOSITION

EXAMPLE 9

| Tablet: preparation formula for 1000 tablets containing 2 mg | |
|---|---|
| (2,2-Dicyclopropylethylidene)aminoguanidine | 2 g |
| Hydroxylpropyl cellulose | 2 g |
| Wheat starch | 10 g |
| Lactose | 100 g |
| Magnesium stearate | 3 g |
| Talc | 3 g |

We claim:

1. A compound of formula (I):

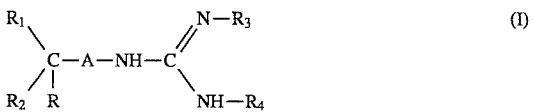

in which:

$R_1$ represents $C_3$-$C_7$ cycloalkyl, $R_2$ represents $C_3$-$C_4$ cycloalkyl, A represents —CH=N—, =N—, or —NH—, $R_3$ and $R_4$, which may be identical or different, represent hydrogen or linear or branched ($C_1$-$C_6$) alkyl, R represents hydrogen in the case where A represents —CH=N—, or —NH—, or a bond selected from those of the group A when A represents =N—, with the proviso, however, that when A is =N— and $R_1$ is a phenyl optionally substituted, $R_2$ does not represent a cycloalkyl ($C_3$-$C_4$), its enantiometers and epimers as well as its addition salts with a pharmaceutically-acceptable acid.

2. A compound as claimed in claim 1, wherein $R_1$ and $R_2$ each represent cyclopropyl, its enantiomers and epimers as well as its addition salts with a pharmaceutically-acceptable acid.

3. A compound as claimed in claim 1, wherein A represents —CH=N—, its enantiomers and epimers as well as its addition salts with a pharmaceutically-acceptable acid.

4. A compound as claimed in claim 1, wherein $R_3$ and $R_4$ each represent hydrogen, its enantiomers and epimers as well as its addition salts with a pharmaceutically-acceptable acid.

5. A compound as claimed in claim 1 which is selected from (2,2-dicyclopropylethylidine)aminoguanidine, and its addition salts with a pharmaceutically-acceptable acid.

6. A method for treating an animal or human living body afflicted with a condition selected from depression, arterial hypertension, and vascular disorders, comprising the step of administering to the living body an amount of a compound of claim 1 which is effective for alleviation of said condition.

7. A pharmaceutical composition useful as an "imidazoline-guanidine" receptor ligand comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,494,934
DATED : February 27 1996
INVENTOR(S) : Charles Malen, Jean-Michel Lacoste, Guillaume de Nanteuil Page 1 of 2

It is certified that error appears in the above-indentified patent and that said Letters Patent is hereby corrected as shown below:

Title Page, Column 1, [56] References Cited, U.S.
    Patent Documents, "3,916,531" should read
    -- 3,816,531 -- and "4,731,393" should read
    -- 4,731,383 --.

Column 1, line 57:  "gorup" should read -- group --.

Column 3, line 23:  "or" should read -- of --.

Column 3, line 45:  "gorup" should read -- group --.

Column 4, line 10:  Add a -- ( -- to beginning of the line.

Column 6, line 31:  "amioguanidine" should read -- aminoguanidine --.

Column 7, line 20:  "30" should read -- 3 --.

UNITED STATES PATENT AND TRADEMARK OFFICE
CERTIFICATE OF CORRECTION

PATENT NO. : 5,494,934
DATED : February 27 1996
INVENTOR(S) : Charles Malen, Jean-Michel Lacoste, Guillaume de Nanteuil It is certified that error appears in the above-indentified patent and that said Letters Patent is hereby corrected as shown below:

Column 8, line 3: "(2-(2-" should read -- 2-(2- --.

Column 10, line 35: "(2,2-dicyclopropylethylidine)" should read -- (2,2-dicyclopropylethylidene) --

Signed and Sealed this

Fourteenth Day of May, 1996

Attest:

BRUCE LEHMAN

*Attesting Officer*    Commissioner of Patents and Trademarks